United States Patent [19]

Johnson et al.

[11] Patent Number: 4,916,678

[45] Date of Patent: Apr. 10, 1990

[54] VISCOMETER

[75] Inventors: Timothy W. Johnson; Marion T. O'Shaughnessy, both of Bartlesville, Okla.

[73] Assignee: Phillips Petroleum Company, Bartlesville, Okla.

[21] Appl. No.: 178,730

[22] Filed: Apr. 7, 1988

Related U.S. Application Data

[62] Division of Ser. No. 295,460, Aug. 24, 1981, Pat. No. 4,750,359, which is a division of Ser. No. 53,446, Jun. 29, 1979, Pat. No. 4,302,965.

[51] Int. Cl.⁴ .......................... G01F 23/00; G04F 8/00
[52] U.S. Cl. .................................. 368/113; 73/304 R
[58] Field of Search ................... 73/55, 304 C, 304 R, 73/290 R; 368/113–114, 118

[56] References Cited

U.S. PATENT DOCUMENTS

| | | | |
|---|---|---|---|
| 3,368,404 | 2/1968 | King | 73/304 R |
| 3,443,438 | 5/1969 | Martin et al. | 73/304 R |
| 3,495,214 | 2/1970 | Wishart | 73/304 R |
| 3,713,328 | 1/1973 | Aritomi | 73/55 |
| 3,798,960 | 3/1974 | Glass | 73/55 |
| 3,964,037 | 6/1976 | Lamphere | 73/304 C |
| 4,010,650 | 3/1977 | Piatkowski et al. | 73/304 C |
| 4,090,408 | 5/1978 | Hedrick | 73/304 C |
| 4,145,927 | 3/1979 | Larson | 73/304 C |
| 4,149,231 | 4/1979 | Bukosky et al. | 73/304 C |

Primary Examiner—Vit W. Miska
Attorney, Agent, or Firm—George E. Bogatie

[57] ABSTRACT

A capillary tube viscometer is provided in which the viscosity of a fluid can be measured at a temperature above the normal boiling point of at least one component in the fluid. The fluid is heated to the desired temperature in a sealed viscometer which is constructed so as to withstand high pressure. The fluid is then allowed to flow through a capillary tube and the time required for the fluid to flow through the capillary tube is measured. The viscosity of the fluid is then calculated based on the Hagen-Poiseuille law.

10 Claims, 3 Drawing Sheets

VISCOMETER

This application is a division of application Ser. No. 295,460 filed Aug. 24, 1981 U.S. Pat. No. 4,750,359, which is a division of application Ser. No. 053,446, filed June 29, 1979, now U.S. Pat. No. 4,302,965.

This invention relates to method and apparatus for measuring viscosity of a fluid. In one aspect this invention relates to method and apparatus for measuring the viscosity of a fluid at temperatures above the normal boiling point of at least one component in the fluid. In another aspect this invention relates to methods and apparatus for determining the level of a liquid.

Viscosity is a fluid property which affects its behavior. If a fluid is defined as being a substance undergoing continuous deformation when subjected to shear stress, then the consistency can be termed the resistance offered by the fluid to such deformation. If static pressure and temperature are fixed, the consistency is constant for gases and Newtonian liquids, and is called absolute viscosity. The consistency of non-Newtonian fluids varies, even though the static pressure and temperature are fixed, as a function of the applied shear stress. In some cases, the consistency may vary with duration of the applied shear stress. The consistency of non-Newtonian fluids is frequently expressed in terms of apparent viscosity. Thus the viscometer is an instrument which measures consistency of gases and Newtonian and non-Newtonian fluids.

Many types of viscometers are known in the art. One well known type is the capillary tube viscometer which consists of a fluid reservoir to hold a specified volume of sample liquid and of a capillary tube. The hydrostatic head of the fluid causes the liquid to flow through the capillary tube. The time required for a fixed fluid volume to flow through the capillary tube is measured and the viscosity of the fluid is calculated based on various physical dimensions of the viscometer and the time required for the fluid to flow through the capillary tube.

The capillary-tube viscometer gives absolute viscosity in Poises from measurements of the pressure gradient and of the volumetric flow-rate in a cylindrical tube of precisely known dimensions as stated by the Poiseuille Law for the flow of fluids through a capillary.

$$\mu = \frac{\pi g h R^4 t \rho}{8 V L} \tag{1}$$

where
- $\mu$ = absolute viscosity, Poises (dyne-sec/cm$^2$)
- $\rho$ = density of liquid, g/cm$^3$
- $g$ = acceleration due to gravity, cm/sec$^2$
- $h$ = length of capillary plus average height of fluid above capillary during time t
- $R$ = radius of capillary, cm
- $L$ = length of capillary, cm
- $V$ = volume of liquid flowing, cm$^3$, in time t, sec.

It is frequently essential to measure the viscosity of a fluid at temperatures above the normal boiling point at atmospheric pressure of at least one component in the fluid. An example of this is a chemical manufacturing process in which the viscosity of a solution must be known to design various apparatus required by the process and determine required operating conditions for the process. It may be that the solvent which is used to make up the solution has a normal boiling point above the temperature at which the process is maintained. It is thus an object of this invention to provide method and apparatus for measuring the viscosity of a fluid at temperatures above the boiling point of at least one component in the fluid.

In an instrument such as a viscometer, as well as in many other applications, it is essential to know when a liquid has reached a particular level. In a viscometer this information is necessary in order to determine the time t which is required for the solution of Equation 1. It is thus an object of this invention to provide methods and apparatus for determining when a liquid has reached a specified level.

In accordance with the present invention, a capillary tube viscometer in the form of a tubular structure is provided. The tubular structure is separated into first and second portions. A pressure equalizing tube and a capillary tube provide the only connections between the first and second portions. Means is provided for rotating the tubular structure with respect to a horizontal axis perpendicular to the longitudinal axis of the tubular structure.

The tubular structure which makes up the viscometer is constructed of a material which will withstand substantial pressure. The tubular structure is first oriented in such a manner that the first portion of the tubular structure is below the second portion of the tubular structure. The first portion of the tubular structure is then filled with a fluid, the first portion is pressure sealed to the second portion, and the temperature of the fluid is raised to a desired level. The tubular structure is then inverted in such a manner that the second portion of the tubular structure will be below the first portion of the tubular structure. The fluid lows through the capillary tube and into the second portion of the tubular structure. Level sensors are provided for determining the time required for the fluid to flow through the capillary tube. The viscosity of the fluid is calculated based on the time required for the fluid to flow through the capillary tube, the size of the fluid sample, and the physical dimensions of the viscometer.

The particular type of level sensor utilized is determined by the conductivity of the fluid flowing through the capillary tube. If the conductivity of the fluid flowing through the capillary tube is low, a capacitive type sensor is preferred. If the conductivity of the fluid flowing through the capillary tube is high, a conductivity type sensor is preferred. A capacitive type sensor is provided in which field-effect transistor oscillators are utilized to start and stop a timing device. The components of the field-effect transistor oscillators are chosen such that the field-effect transistor oscillators oscillate only when liquid covers the capacitive sensors in the viscometer. These oscillations are used to either start or stop a timing device depending on which capacitive sensor has been covered by the fluid.

A conductivity type level detector is provided in which the output from a comparator is utilized to either start or stop a timing device. A first conductivity sensor is utilized to start the timing device when fluid covers the first conductivity sensor by forcing the output from the comparator to a first state. A second conductivity sensor is utilized to stop the timing device when liquid covers the second conductivity sensor by driving the output of the comparator to a second state.

Other objects and advantages of the invention will be apparent from the foregoing brief description of the invention and the claims as well as from the detailed description of the drawings in which:

Figure 1:
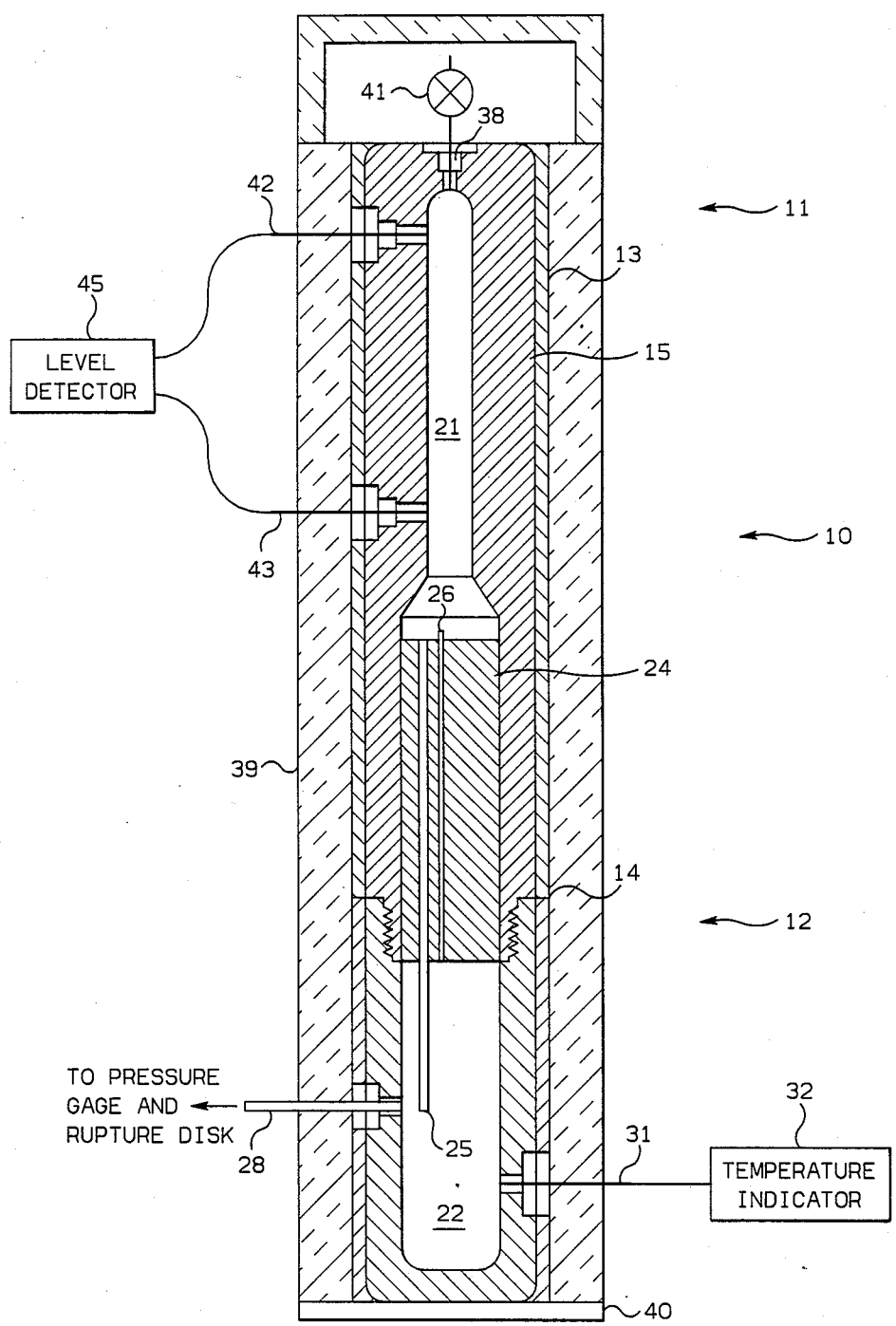
FIG. 1 is a diagrammatic representation in cross-section of the viscometer of the present invention.

Referring now to the drawings, and in particular to FIG. 1, a viscometer 10 is illustrated having an upper section 11 and a lower section 12. The upper section 11 is joined to the lower section 12 by the threaded joint 14. The inner portion 15 of the viscometer 10 is preferably formed from stainless steel or some other suitable material capable of withstanding high pressure The inner portion 15 of the viscometer 10 is enclosed by the jacket 13 which is preferably formed rom aluminum. A tubular opening 21 is formed in the upper section 11 of the viscometer 10. A tubular opening 22 is formed in the lower section 12 of the viscometer 10. The tubular opening 21 is separated from the tubular opening 22 by a partition 24 which is preferably formed from aluminum.

Means not illustrated, but obvious to one skilled in the art, is provided to support the viscometer 10 and to permit rotation of the viscometer 10. The viscometer 10 may be rotated with respect to a horizontal axis perpendicular to the vertical axis, as illustrated in FIG. 1, of the viscometer 10. The viscometer 10 may be rotated so as to place the tubular opening 21 substantially above the tubular opening 22 or to place the tubular opening 22 substantially above the tubular opening 21.

A pressure equalization tube 25 and a capillary tube 26 extend through the partition 24. Both the pressure equalization tube 25 and the capillary tube 26 are preferably formed from stainless steel. Conduit means 28 provides a means for measuring the pressure in the viscometer 10 and also provides a means for relieving pressure in the viscometer 10 if the pressure in the viscometer 10 should become higher than the viscometer 10 was designed to withstand. A thermocouple 31, which is operably located so as to sense the temperature in the tubular opening 22, provides a signal representative of the temperature in the tubular opening 22 to the temperature indicator 32. Sensors 42 and 43, which are operably located so as to be exposed to any fluid in the tubular opening 21, provide output signals to the level sensing sensor 45 which are utilized to determine the time required for a fluid to flow through the capillary tube 26.

The upper section 11 and the lower section 12 of the viscometer 10 is preferably surrounded by an insulating jacket 39 which is preferably formed from steel and silica insulating material. A heater 40, which preferably incorporates a magnetic stirrer, provides heat for the fluid contained in the lower section 12 of the viscometer 10. When the heater 40 is not being utilized, the heater 40 is removed and the lower portion of the lower section 12 is covered with the insulating material from which the jacket 39 is formed. Fluid contained in the upper portion 11 can be drained by opening the control valve 41 which is operably located in conduit means 38. Control valve 41 is normally maintained in a closed position.

Any desire diameter and length for the capillary tube 26 can be utilized. The preferred diameter of the capillary tube is determined based on the viscosity of the fluid in the viscometer. The ratio of capillary length to diameter should be kept as large as possible. The ratio of capillary length to diameter should be at least about 25 and, more preferably, should be greater than 50.

In operation, the upper section 11 of the viscometer 10 is removed from the lower section 12. A fluid, the viscosity of which is to be determined, is then placed in the tubular opening 22. The upper level of the fluid to be analyzed will generally extend slightly above the thermocouple 31. After the fluid has been placed in the tubular opening 22, the upper portion 11 of the viscometer 10 is again attached to the lower portion 12 to pressure seal the viscometer. The fluid is then heated to a desired temperature.

The pressure in the viscometer 10 will rise as the temperature of the fluid is increased. The pressure will continue to rise until the temperature at which the viscosity of the fluid is to be measured is reached. The pressure will vary depending upon the fluid to be analyzed. The viscometer 10 is preferably constructed to withstand at least 500 psi.

After the fluid contained in the tubular opening 22 has been heated to a desired temperature, the viscometer 10 is very quickly rotated with respect to a horizontal axis, as illustrated in FIG. 1, in such a manner that the upper section 11 will be located preferably directly below the lower section 12. The hydrostatic head of the fluid in the tubular opening 12 will cause the fluid to flow through the capillary 26. It is noted that the pressure equalization tube 25 extends into the tubular opening 22 for a distance sufficient to prevent the fluid in the tubular opening 22 from flowing through the pressure equalization tube 25 when the viscometer is inverted.

The time required for the fluid flowing into the tubular opening 21 to rise from sensor 42 to sensor 43 is measured by the level detection circuit 45. The viscosity of the fluid can then be calculated based on equation (I). The manner in which the viscosity is calculated will be described more fully in the examples.

The conductivity of the fluid flowing in the viscometer generally determines the type of level sensing which must be utilized. If the conductivity is low, then a capacitive type level sensor is preferred. If the conductivity is high, a conductivity type level sensor is preferred.

Sensors 42 and 43 are typical insulated feed through devices which are commercially available as will be more fully described hereinafter. The sensors 42 and 43 may serve as either capacitive sensors when utilized in the circuit illustrated in FIG. 2 or conductivity sensors when utilized in the circuit illustrated in FIG. 3.

Figure 2:
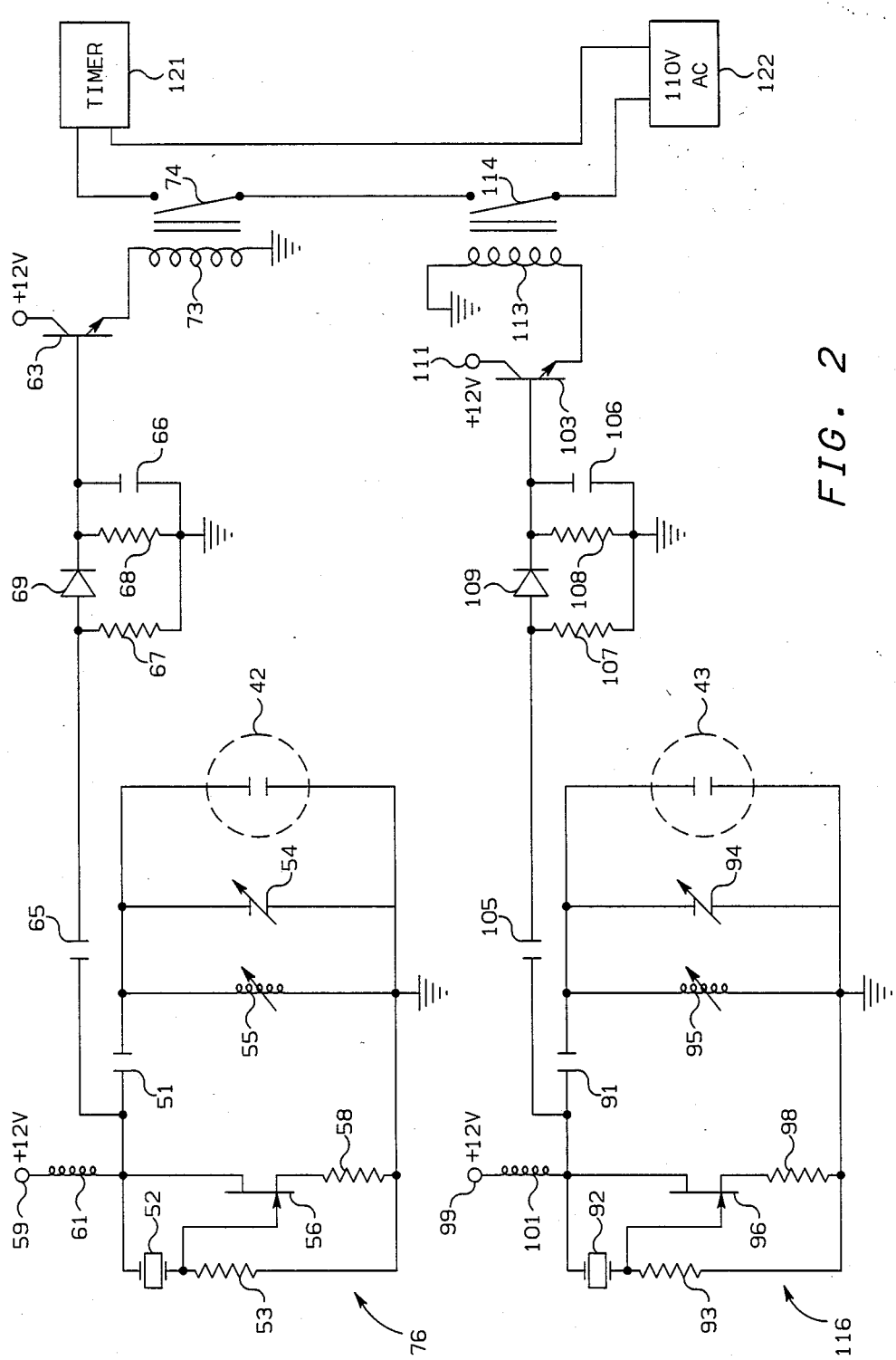
FIG. 2 is a schematic representation of a capacitive level sensor circuit utilized to measure the time required for the fluid to flow through the capillary tube of the viscometer.

Referring now to FIG. 2, a capacitive level sensor circuit which can be utilized for the level detector 45 is illustrated. Variable capacitor 54 and variable inductor 55 are connected in parallel with the capacitive sensor 42. The crystal 52 is connected to ground through resistor 53. The gate of the field-effect transistor 56 is connected to the crystal 52 and is also connected to ground through resistor 53. The source of the field-effect transistor 56 is connected to ground through resistor 58. The drain of the field-effect transistor 56 is tied to the +12 volt power supply 59 through inductor 61 and is tied to the crystal 52.

The field-effect transistor 56 and the crystal 52 together with the inductor 61, resistors 53 and 58, variable inductor 55, variable capacitor 54 and the capacitive sensor 42 form a field-effect transistor oscillator 76. The field-effect transistor oscillator 76 is a capacitive sensitive circuit in which oscillations are not sustained unless there is sufficient capacitance in the tank circuit made up of capacitor 51, variable capacitor 54, variable inductor 55 and the capacitive sensor 42. The values for capacitors 51, variable capacitor 54 and variable inductor 55 are selected in such a manner that the field-effect transistor oscillator will not oscillate unless the fluid in the tubular opening 21 rises above the capacitive sensor 42. When the fluid in the tubular opening 21 does rise above the capacitive sensor 42, sufficient capacitance is provided to turn on the field-effect transistor oscillator 76. The turn-on capacitance is very well defined and the oscillator 52 turns on virtually instantaneously when the fluid rises above the capacitive sensor 42.

The field-effect transistor oscillator 76 is electrically connected to the base of the transistor 63 through the combination of capacitors 65 and 66, resistors 67 and 68 and diode 69. The collector of the transistor 63 is tied to the +12 volt power supply 71. The emitter of the transistor 63 is electrically connected through the relay 73, which energizes the normally open switch 74, to ground.

The oscillations from the field-effect transistor oscillator 76 are provided through the coupling capacitor 65 and are rectified by the diode 69. The resistors 67 and 68 together with the capacitor 66 provide capacitive filtering for the signal provided to the base of the transistor 63. The transistor 63 is turned on when the field-effect transistor oscillator 76 is turned on and this has the effect of energizing the relay 73 which in turn closes the normally open switch 74.

Variable capacitor 94 and variable inductor 95 are connected in parallel with the capacitive sensor 43. The crystal 92 is connected to ground through resistor 93. The gate of the field-effect transistor 96 is connected to the crystal 92 and is also connected to ground through resistor 93. The source of the field-effect transistor 96 is connected to ground through resistor 98. The drain of the field-effect transistor 96 is tied to the +12 volt power supply 99 through inductor 101 and to the crystal 52.

The field-effect transistor 96 and the crystal 92 together with the inductor 101, resistors 93 and 98, variable inductor 95, variable capacitor 94 and the capacitive sensor 43 form a field-effect transistor oscillator 116. The values for capacitors 91, variable capacitor 94 and variable inductor 95 are selected in such a manner that the field-effect transistor oscillator will not oscillate unless the fluid in the tubular opening 21 rises above the capacitive sensor 43. When the fluid in the tubular opening 21 does rise above the capacitive sensor 43, sufficient capacitance is provided to turn on the field-effect transistor oscillator 116.

The field-effect transistor oscillator 116 is electrically connected to the base of the transistor 103 through the combination of capacitors 105 and 106, resistors 107 and 108 and diode 109. The collector of the transistor 103 is tied to the +12 volt power supply 111. The source of the transistor 103 is electrically connected through the relay 113, which energizes the normally closed switch 114, to ground.

The oscillations from the field-effect transistor oscillator 116 are provided through the coupling capacitor 105 and are rectified by the diode 109. The resistors 107 and 108 together with the capacitor 106 provide capacitive filtering for the signal provided to the base of the transistor 103. The transistor 103 is turned on when the field-effect transistor oscillator is turned on and this has the effect of energizing the relay 113 which in turn opens the normally closed switch 114.

The timer 121 is powered from a typical 110 volt wall outlet 122. The normally open switch 74 and the normally closed switch 114 are electrically connected in the line which powers the timer 121. In operation, the normally open switch 74 will be closed when the fluid rises above the capacitive sensor 42. This will have the effect of starting the timer 121. The normally closed switch 114 will be opened when the fluid rises above the capacitive sensor 43. This will have the effect of stopping the timer 121. Thus the time shown on the timer 121 will provide an indication of the time required for the fluid in the viscometer to fill the volume of the opening 21 between the capacitive sensor 42 and the capacitive sensor 43.

It is noted that only one capacitive sensor and only one field-effect transistor oscillator circuit could be utilized to detect when a liquid is at a particular level. The oscillations could drive an alarm circuit or other similar device to provide an indication of the fact that a liquid has risen to, is presently at, has fallen below some particular level, or is flowing past a particular point.

Electrical components which can be utilized in the circuit illustrate in FIG. 2 are as follows:

| | |
|---|---|
| Transistors 56, 96 | 2N3823 |
| | Motorola Semiconductor |
| Transistors 74, 114 | 2N1304 |
| | Motorola Semiconductor |
| Diodes 69, 109 | 1N914 |
| | Motorola Semiconductor |
| Crystals 52, 96 | 433215 (5 MHz) |
| | International Crystal Manufacturing Co. |
| Inductors 61, 101 | 4669-E (5.5 mh) |
| | J. W. Miller; Co. |
| Variable inductors 55, 95 | 4406 (7.3 to 14 ph) |
| | J. W. Miller, Co. |
| Variable capacitors 54, 94 | MA-2 (3 to 40 pf) |
| | J. W. Miller, Co. |
| Sensors 42, 43 | EG-093-A-SS-L |
| | Conax Corp. |
| Relays 74, 114 | 12 Vdc coil, 10 ma |
| | Radio Shack |
| Resistors 53, 93, 67, 107 | 420 K ohm, 1/4W |
| | Dale |
| Resistors 58, 98 | 1 K ohm, 1/4W |
| | Dale |
| Resistors 68, 108 | 1 M ohm, 1/4W |
| | Dale |
| Capacitors 51, 91 | 100 picofarad |
| | Sprague |
| Capacitors 65, 105 | 10 picofarad |
| | Sprague |
| Capacitors 66, 106 | 50 picofarad |
| | Sprague |
| Timer 121 | S10 |
| | Standard Electric Time Co. |

Figure 3:
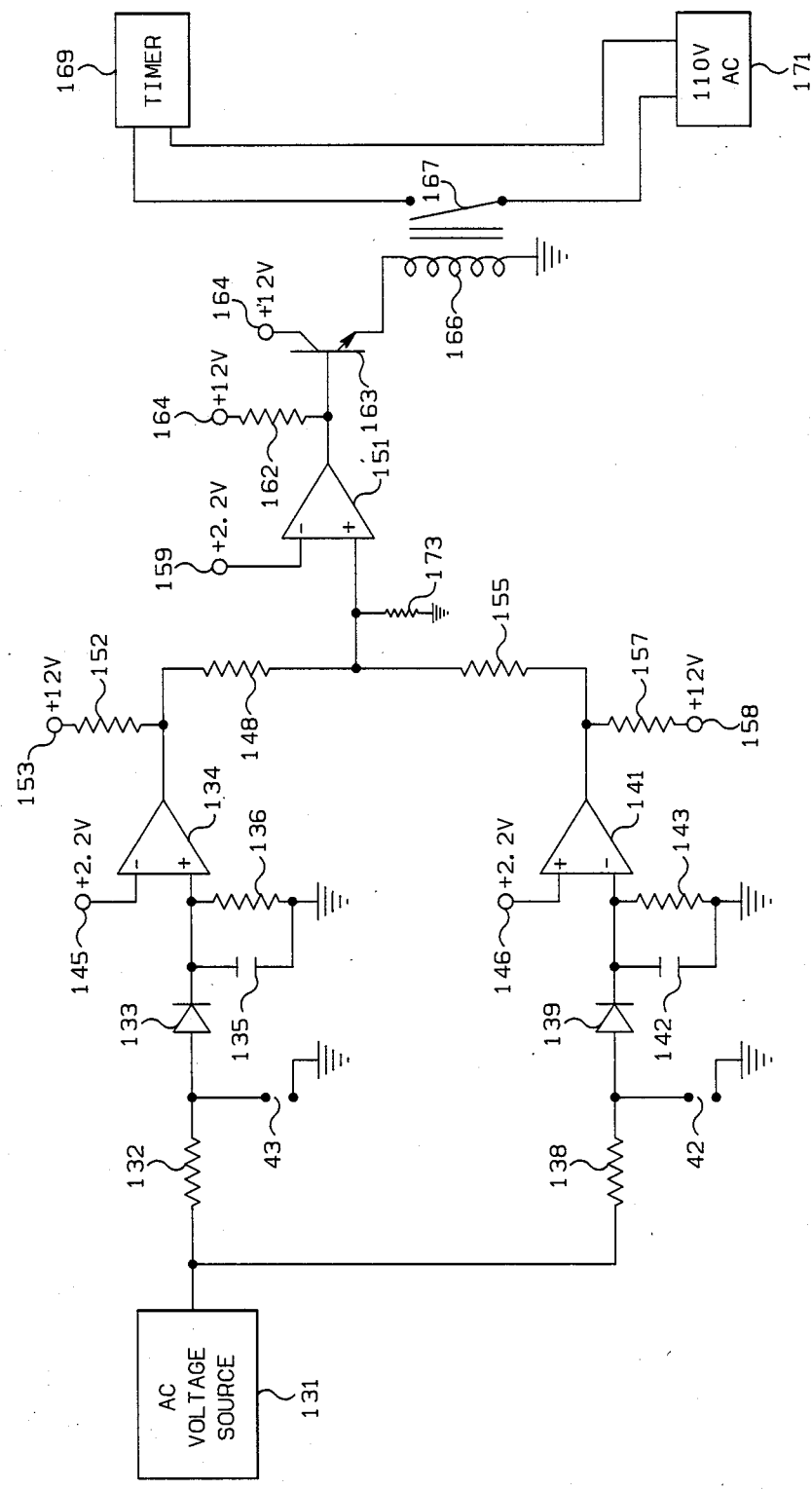
FIG. 3 is a schematic representation of a conductivity level sensor circuit utilized to measure the time required for the fluid to flow through the capillary tube of the viscometer.

Referring now to FIG. 3, a conductivity type level sensor circuit which can be utilized for the level detector 45 is illustrated. The AC voltage source 131 provides an AC voltage through resistor 132 and diode 133 to the non-inverting input of the operational amplifier 134. The parallel combination of the capacitor 135 and the resistor 136 acts as a filter. The diode 133 acts as a rectifier while the conductivity sensor 43 provides a path to ground for the signal provided from the AC voltage source 131 when liquid rises above sensor 43. In like manner, the AC voltage source provides an AC voltage through the resistor 138 and the diode 139 to the inverting input of the operational amplifier 141. The parallel combination of the capacitor 142 and the resistor 143 acts as a filter. The diode 139 acts as a rectifier. The conductivity sensor 42 provides a path to ground for the AC signal provided from the voltage source 131 to the operational amplifier 141 when liquid rises above the sensor 42.

The inverting input of the operational amplifier 134 is tied to the +2.2 volt power supply 145. The non-inverting input of the operational amplifier 141 is tied to the +2.2 volt power supply 146. The output of the operational amplifier 134 is tied through resistor 148 to the non-inverting input of the operational amplifier 151. The output of the operational amplifier 134 is also tied through resistor 152 to the +12 volt power supply 153. The output of the operational amplifier 141 is tied through resistor 155 to the non-inverting input of the operational amplifier 151. The non-inverting input of operational amplifier 151 is also tied to ground through resistor 173. The output of the operational amplifier 141 is also tied through resistor 157 to the +12 volt power supply 158.

The non-inverting input of the operational amplifier 151 is tied to the +2.2 volt power supply 159. The output of the operational amplifier 151 is supplied to the base of the transistor 163 and is also tied through resistor 162 to the +12 volt power supply 160. The +2.2 power supplies 145, 146 and 159 will typically be the same power source and may be referred to as the reference power source.

The collector of the transistor 163 is tied to the +12 volt power supply 164. The source of the transistor 163 is electrically connected through the relay 166, which energizes the normally open switch 167, to ground. The +12 volt power supplies 153, 158, 160 and 164 will typically be the same power source.

The timer 169 is powered from a typical 110 volt wall outlet 171. The normally open switch 167 is electrically connected in the line which powers the timer 169. In operation, the timer 169 starts when liquid contacts conductivity sensor 42 and stops when liquid contacts conductivity sensor 43. The operational amplifiers 134, 141 and 151 are configured as comparators. The output from the operational amplifiers 134, 141 and 151 will either be 0 or 10 volts. When the liquid contacts sensor 42 but does not contact sensor 43, the output from both the operational amplifier 134 and the operational amplifier 141 will be approximately 10 volts. Input to the non-inverting input of the operational amplifier 151 will be approximately 2.6 volts and the output of the operational amplifier 151 will be approximately 10 volts. This 10 volt output will turn the timer 161 on when liquid contacts the sensor 42 by turning on the transistor 163 which will in turn energize the relay 166 to close the normally open switch 167. When liquid contacts both the sensor 42 and the sensor 43, the output of operational amplifier 134 will go to approximately 0 volts. The output of the operational amplifier 141 will stay at 10 volts. Approximately 1.3 volts will be provided to the non-inverting input of the operational amplifier 151 and the output of the operational amplifier 151 will go to 0 volts. This will have the effect of turning the timer 161 off when liquid contacts the sensor 43 by turning off the transistor 163 which deenergizes the switch 167 allowing the normally open switch 167 to return to its normally open position.

It is noted that only one comparator in combination with one conductivity sensor could be utilized to detect when a liquid is at a particular level. The output of the comparator could be utilized to drive an indicating circuit, such as a light, an alarm circuit or other similar device to provide an indication of the fact that a liquid has risen to, is presently at, has fallen below some particular level, or is flowing past a particular point.

| | |
|---|---|
| Operational Amplifiers 134, 141, 151 | LM339 National Semiconductor |
| Diodes 133, 139 | 1N914 Motorola Semiconductor |
| Resistors 152, 157, 162, 132, 138 | 10 K ohm Dale |
| Resistors 148, 155 | 100 K ohm Dale |
| Resistor 173 | 18 K ohm Dale |
| Capacitors 135, 142 | 0.1 microfarad Sprague |
| AC voltage source | 3 V RMS, 1200 Hz |
| Relay 166 | 12 Vdc coil, 10 ma Radio Shack |
| Sensors 42, 43 | EG-093-A-SS-L Conax Corp. |
| Timer 169 | S1O Standard Electric Timer Corp. |

The values of resistors 132 and 138 may typically be 10 K ohm. However, for proper operation of the level sensing circuits illustrated in FIG. 3, the values of resistor 132 and 138 should be adjusted to approximate the sum of the conductivity of the liquid in the viscometer and the cell constant of the conductivity sensors.

The following examples are presented in further illustration of the invention.

EXAMPLE I

A capillary tube having a diameter of 0.163 cm and length of 13.1 cm was used to measure the viscosity of a solution of Ryton ® polyphenylene sulfide (sold by Phillips Petroleum Co. of Bartlesville, Okla.) and N-methylpyrrolidone. The normal boiling point of the N-methylpyrrolidone is 202° C. at standard pressure. 16.1 grams of Ryton ® polyphenylene sulfide was dissolved in 59.0 grams of N-methylpyrrolidone and the solution was then placed in the lower portion 12 of the viscometer 10. The viscometer 10 was pressure sealed and the solution was heated to 262° C. The viscometer 10 was then rotated with respect to its horizontal axis. The conductivity type level sensor illustrated In FIG. 3 was utilized because of the high conductivity of the solution of Ryton ® polyphenylene sulfide and N-methylpyrrolidone. Relevant parameters required for the solution of Equation (1) are as follows:

$\rho = 0.89$ g/cm$^3$
g = 980 cm/sec$^2$
h = 18.0 cm
R = 0.0816 cm
L = 13.1 cm
t = 341 sec The volume utilized is the volume of the opening 21 between the sensors 42 and 43. The volume V was 51.9 cm3.

Substituting these values into Equation I gives a calculated absolute viscosity of 0.106 Poise.

EXAMPLE II

A capillary tube having a diameter of 0.163 cm and a length of 13.1 cm was used to measure the viscosity of a solution of Ryton ® polyphenylene sulfide and N-methylpyrrolidone. 22.5 grams of the Ryton ® polyphenylene sulfide was dissolved in 52.5 grams of N- methylpyrrolidone and the solution was then placed in the lower portion 12 of the viscometer 10. The viscometer 10 was pressure sealed, the solution was heated to 262° C., and the viscometer 10 was then rotated with respect to its horizontal axis. Relevant parameters required for the solution of Equation (I) are as follows:

$p = 0.92 \text{ g/cm}^3$
$g = 980 \text{ cm/sec}^2$
$h = 18.0 \text{ cm}$
$R = 0.0816 \text{ cm}$
$L = 13.1 \text{ cm}$
$L = 911 \text{ sec}$
$V = 51.9 \text{ cm}^3$ Substituting these values into Equation (I) gives a calculated absolute viscosity of 0.366 Poise.

While the invention has been described in terms of the presently preferred embodiment, reasonable variations and modifications are possible by those skilled in the art, within the scope of the described invention and the appended claims. Variations such as using a different timing device to determine when the fluid level rises above the sensor 43 illustrated in FIG. 1 is within the scope of the invention. Further, variations in the dimensions or physical configuration of the viscometer are within the scope of the invention.

That which is claimed is:

1. A method for measuring the elapsed time between the time a fluid contacts a first conductivity sensor and the time said fluid contacts a second conductivity sensor comprising the steps of:
   driving a first comparator to a first output state when said fluid contacts said first conductivity sensor;
   driving said first comparator to a second output state when said fluid is not contacting said first conductivity sensor;
   driving a second comparator to said first output state when said fluid is not contacting said second conductivity sensor;
   driving said second comparator to said second output state when said fluid contacts said second conductivity sensor;
   driving the output of a third comparator to said first output state when both said first comparator and said second comparator are in said first output state to thereby start a timing device; and
   driving said third comparator to said second output state when said first comparator is in said first output state and said second comparator is in said second output state to thereby stop said timing device, the time indicated on said timing device providing a determination of the elapsed time between the time said fluid contacts said first conductivity sensor and the time said fluid contacts said second conductivity sensor.

2. Apparatus comprising:
   a first conductivity sensor;
   a second conductivity sensor;
   first comparator means having first and second inputs and an output;
   means for electrically connecting a first input of said first comparator means to said first conductivity sensor;
   means for connecting the second input of said first comparator means to a power supply;
   a second comparator means having first and second inputs and an output;
   means for electrically connecting a first input of said first comparator means to said second conductivity sensor;
   means for electrically connecting the second input of said comparator means to said first power supply;
   a third comparator means having first and second inputs and an output;
   means for electrically connecting the output of said first comparator means and the output of said second comparator means to a first input of said third comparator means;
   means for connecting the second input of said third comparator means to said power supply;
   a timing means; and
   means for supplying output of said third comparator means to said timing means, said timing means being initiated when the fluid contacts said first conductivity sensor so as to reduce the voltage level at the first input of first comparator means, said timing means being stopped when said fluid contacts said second conductivity sensor so as to reduce the voltage level at the first input terminal of said second comparator means, the time indicated by said timing means providing a measurement of the elapsed time between the time a fluid contacts said first conductivity sensor and the time said fluid contacts said second conductivity sensor.

3. Apparatus comprising:
   a first conductivity sensor;
   a second conductivity sensor;
   a first voltage source;
   a first operational amplifier having a non-inverting input, an inverting input and an output;
   a second voltage source;
   means for electrically connecting the non-inverting input of said first operational amplifier to said second voltage source;
   means for electrically connecting the inverting input of said first operational amplifier to said first conductivity sensor;
   a second operational amplifier having a non-inverting input, an inverting input and an output;
   means for electrically connecting said first voltage source to the non-inverting input of said second operational amplifier;
   means for electrically connecting the non-inverting input of said second operational amplifier to said second conductivity sensor;
   means for electrically connecting the inverting input of said second operational amplifier to said second voltage source;
   a third operational amplifier having a non-inverting input, an inverting input and an output;
   means for electrically connecting the output of said first operational amplifier and the output of said second operational amplifier to the non-inverting input of said third operational amplifier;
   means for electrically connecting the inverting input of said third operational amplifier to said second voltage source;
   a timing means; and
   means for initiating said timing means when the output o: said third operational amplifier is in a first state and for stopping said timing means when the output of said third operational amplifier is in a second state, the output of said third operational amplifier being in said first state when fluid contacts said first conductivity sensor so as to reduce the voltage level at the inverting input of said first operational amplifier and said fluid is not above said second conductivity sensor and the voltage level at the non-inverting input of said second operational amplifier is not reduced, the output of said third operational amplifier being in said second state when said fluid covers said first conductivity sensor so as to reduce the voltage level at the inverting input of said first operational amplifier and said fluid covers said second conductivity sensor so as to reduce the voltage level at the non-inverting input of said second operational amplifier, the time indicated by said timing means providing a measurement of the elapsed time between the time said fluid contacts said first conductivity sensor and the time said fluid contacts said second conductivity sensor.

4. Apparatus comprising:
a conductivity sensor;
a first voltage source;
an operational amplifier having a non-inverting input, an inverting input and an output;
means for electrically connecting said first voltage source to the inverting input of said operational amplifier;
means for electrically connecting the inverting input of said operational amplifier to said conductivity sensor;
a second voltage source; and
means for electrically connecting the non-inverting input of said operational amplifier to said second voltage source, the output of said operational amplifier being in a first state when a fluid contacts said conductivity sensor so as to reduce the voltage level at the inverting input of said operational amplifier, the output of said operational amplifier being in a second state when said fluid is not in contact with said conductivity sensor, the output state of said operational amplifier providing an indication of whether or not said fluid is contacting said conductivity sensor.

5. Apparatus in accordance with claim 4 wherein said first voltage source is a direct current voltage source and said second voltage source is an alternating current voltage source.

6. Apparatus comprising:
a conductivity sensor;
a first voltage source;
an operational amplifier having a non-inverting input, an inverting input and an output;
means for electrically connecting said first voltage source to the non-inverting input of said operational amplifier;
means for electrically connecting the non-inverting input of said first operational amplifier to said conductivity sensor;
a second voltage source; and
means for electrically connecting the inverting input of said operational amplifier to said second voltage source, the output of said operational amplifier being in a first state when a fluid contacts said conductivity sensor so as to reduce the voltage level at the non-inverting input of said operational amplifier, the output of said operational amplifier being in a second state when said fluid is not in contact with said conductivity sensor, the output state- of said operational amplifier providing an indication of whether or not said fluid is contacting said conductivity detector.

7. Apparatus in accordance with claim 6 wherein said first voltage source is a direct current voltage source and said second voltage source is an alternating current voltage source.

8. Apparatus comprising:
a conductivity sensor;
an alternating current voltage source for generating an AC signal;
means, operatively interconnecting said conductivity sensor and said alternating current voltage source, for applying said AC signal to said conductivity sensor wherein said conductivity sensor provides a path to ground for said AC signal when fluid is in contact with said conductivity sensor;
circuit means, electrically connected to said conductivity sensor, for producing a rectified signal;
differential-amplifier type of comparator means having a pair of inputs and an output for providing an output signal at said output in response to signals applied to said pair of inputs;
means for electrically connecting said rectified signal to one of said pair of inputs;
and means for electrically connecting the other one of said pair of inputs to a direct current voltage supply, said output signal of said comparator providing an indication of when fluid is in contact with said conductivity sensor.

9. Apparatus in accordance with claim 8 wherein said circuit means comprises:
a rectifier element and a filter element serially connected so as to have a circuit mode therebetween; and
means for connecting said circuit means in parallel arrangement with said conductivity sensor, wherein said rectifier signal appears at said circuit node.

10. In an apparatus including a conductivity sensor and a differential-amplifier type of comparator having a pair of inputs and an output, a method of indicating when fluid is in contact with said conductivity sensor, said method comprising the steps of:
applying an AC signal voltage to said conductivity sensor, said conductivity sensor providing a path to ground for said AC signal voltage when fluid contacts said conductivity sensor;
connecting a serially connected rectifier element and filter element, having a circuit node between said rectifier element and said filter element, in parallel with said conductivity sensor, wherein a rectified signal voltage appears at said circuit node;
applying said rectified signal voltage to one of the inputs of said differential-amplifier type comparator; and
applying a direct current voltage supply to the other input of said differential-amplifier type comparator, the output of said differential-amplifier type comparator providing an indication of when fluid is in contact with said conductivity sensor.

* * * * *